United States Patent
Oh et al.

(10) Patent No.: US 12,401,063 B2
(45) Date of Patent: Aug. 26, 2025

(54) LITHIUM SECONDARY BATTERY

(71) Applicant: LG Energy Solution, Ltd., Seoul (KR)

(72) Inventors: Jeong Woo Oh, Daejeon (KR); Ha Eun Kim, Daejeon (KR); Chul Haeng Lee, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 584 days.

(21) Appl. No.: 17/942,381

(22) Filed: Sep. 12, 2022

(65) Prior Publication Data

US 2023/0085811 A1    Mar. 23, 2023

(30) Foreign Application Priority Data

Sep. 14, 2021  (KR) .................. 10-2021-0122325

(51) Int. Cl.
*H01M 10/0567* (2010.01)
*C07D 233/90* (2006.01)
*H01M 4/02* (2006.01)
*H01M 4/48* (2010.01)
*H01M 4/505* (2010.01)
*H01M 4/525* (2010.01)
*H01M 4/587* (2010.01)
*H01M 10/0568* (2010.01)
*H01M 10/0569* (2010.01)

(52) U.S. Cl.
CPC ...... *H01M 10/0567* (2013.01); *C07D 233/90* (2013.01); *H01M 10/0568* (2013.01); *H01M 10/0569* (2013.01); *H01M 2004/027* (2013.01); *H01M 2004/028* (2013.01); *H01M 4/483* (2013.01); *H01M 4/505* (2013.01); *H01M 4/525* (2013.01); *H01M 4/587* (2013.01); *H01M 2300/0037* (2013.01)

(58) Field of Classification Search
CPC ......... H01M 10/0567; H01M 10/0568; H01M 10/0569; H01M 2300/0037; C07D 233/54
USPC ........................................... 429/332
See application file for complete search history.

(56) References Cited

U.S. PATENT DOCUMENTS

| | | | |
|---|---|---|---|
| 2010/0229950 A1 | 9/2010 | Kuang et al. | |
| 2015/0200422 A1 | 7/2015 | Lee et al. | |
| 2019/0334207 A1 | 10/2019 | Yu et al. | |
| 2020/0044287 A1 | 2/2020 | Kim et al. | |
| 2020/0185774 A1* | 6/2020 | Cho | H01M 10/0567 |
| 2020/0251777 A1* | 8/2020 | Lim | C07D 233/58 |
| 2020/0308149 A1 | 10/2020 | Polishak | |
| 2022/0115701 A1* | 4/2022 | An | H01M 4/364 |
| 2022/0140391 A1* | 5/2022 | Kim | C07D 233/90 429/188 |
| 2022/0393240 A1* | 12/2022 | Oh | H01M 10/0525 |

FOREIGN PATENT DOCUMENTS

| | | |
|---|---|---|
| EP | 3518334 A1 | 7/2019 |
| JP | 2002249579 A | 9/2002 |
| JP | 2005108664 A | 4/2005 |
| JP | 2013251137 A | 12/2013 |
| JP | 2021057330 A | 4/2021 |
| KR | 20090003215 A | 1/2009 |
| KR | 20150085670 A | 7/2015 |
| KR | 20180086601 A | 8/2018 |
| KR | 20190008100 A | 1/2019 |
| KR | 102103898 B1 | 4/2020 |
| KR | 20200092889 A | 8/2020 |
| KR | 20200105227 A | 9/2020 |
| KR | 102179846 B1 | 11/2020 |
| KR | 20210083067 A | 7/2021 |
| WO | 2019126548 A1 | 6/2019 |

OTHER PUBLICATIONS

Michelle J. MacLeod and Jeremiah A. Johnson, "PEGylated N-Heterocyclic Carbene Anchors Designed to Stabilize Gold Nanoparticles in Biologically Relevant Media", Jun. 17, 2015, J. Am. Chem. Soc., 137, 7974-7977 (Year: 2015).*
Extended European Search Report for Application No. 22870222.1 dated May 7, 2025. 5 pages.

* cited by examiner

*Primary Examiner* — Allison Bourke
*Assistant Examiner* — Robert Gene West
(74) *Attorney, Agent, or Firm* — Lerner David LLP

(57) ABSTRACT

A non-aqueous electrolyte solution for a lithium secondary battery, and a lithium secondary battery including the same are disclosed herein. In some embodiments, the non-aqueous electrolyte solution for a lithium secondary battery includes a lithium salt, an organic solvent, and a compound represented by the following Formula 1, and has an excellent effect of scavenging decomposition products generated from the lithium salt, and thus, may improve overall performance of the battery:

[Formula 1]

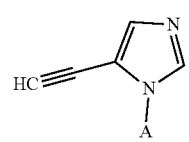

wherein in Formula 1,
A is a C1 to C5 alkyl group.

15 Claims, No Drawings

LITHIUM SECONDARY BATTERY

CROSS-REFERENCE TO RELATED APPLICATIONS

The present application claims priority from Korean Patent Application No. 10-2021-0122325, filed on Sep. 14, 2021, the disclosure of which is incorporated herein by reference.

BACKGROUND OF THE INVENTION

The present disclosure provides a non-aqueous electrolyte solution for a lithium secondary battery, and a lithium secondary battery including the same. More specifically, the present disclosure relates to a non-aqueous electrolyte solution for a lithium secondary battery including an electrolyte solution additive for a secondary battery, the electrolyte solution additive having an excellent effect of scavenging decomposition products generated from a lithium salt, and a lithium secondary battery including the non-aqueous electrolyte solution.

As personal IT devices and computer networks have been developed due to the development of an information society and the society's reliance on electric energy is increased overall, there is a need for the development of a technology for efficiently storing and utilizing electric energy.

Since secondary batteries may be made small enough to be applied to personal IT devices and the like, and may be applied to electric vehicles, power storage devices, and the like, there have been growing interests in the secondary batteries as being the most suitable technology for various applications. Among secondary batteries, a lithium ion battery (LIB), which is a battery system having a high energy density, is under the spotlight and is currently being applied to various devices.

The lithium ion battery is composed of a positive electrode made of a transition metal oxide containing lithium, a negative electrode capable of storing lithium, an electrolyte solution including an organic solvent containing a lithium salt, and a separator.

Meanwhile, in order to implement suitable properties of a battery, the lithium ion battery mainly uses $LiPF_6$ as a representative lithium salt. However, since the $LiPF_6$ is very vulnerable to heat, when the battery is exposed to a high temperature, the $LiPF_6$ is thermally decomposed and generates a Lewis acid such as $PF_5$. Such a Lewis acid material not only causes a decomposition reaction of an organic solvent such as ethylene carbonate, but also deteriorates a film such as a solid electrolyte interphase (SEI) formed on the surface of an electrode, resulting in an additional electrolyte solution decomposition reaction and transition metal elution from a positive electrode.

The eluted transition metal ions are re-deposited on the positive electrode and cause the resistance of the positive electrode to increase, or on the contrary, are transferred to a negative electrode through the electrolyte solution, and then deposited on the negative electrode and cause the additional consumption of lithium ions due to self-discharge of the negative electrode, or destruction and regeneration of the solid electrolyte interphase (SEI) film, and the like, resulting in being a cause to increase resistance, deteriorate lifespan, and the like.

Therefore, in order to suppress the deterioration behavior of a battery when the battery is exposed to a high temperature, there have been growing interests in methods capable of scavenging by-products such as HF and $PF_5$ which are generated due to the thermal decomposition of a lithium salt, and at the same time, improving the passivation capability of an SEI film.

PRIOR ART DOCUMENT

Patent Document

Japanese Patent Laid-Open Publication No. 2005-108664

BRIEF SUMMARY OF THE INVENTION

An aspect of the present disclosure provides a non-aqueous electrolyte solution for a lithium secondary battery, the non-aqueous electrolyte solution capable of implementing excellent high-temperature stability and high-temperature cycle properties by including an electrolyte solution additive for a secondary battery, the electrolyte solution additive capable of scavenging decomposition products generated from a lithium salt, and at the same time, implementing an effect of enhancing an SEI, and a lithium secondary battery including the non-aqueous electrolyte solution.

According to an aspect of the present disclosure, there is provided a non-aqueous electrolyte solution for a lithium secondary battery, the non-aqueous electrolyte solution including a lithium salt, an organic solvent, and a compound represented by Formula 1 below.

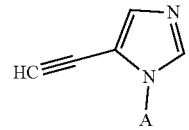

[Formula 1]

In Formula 1, A is a C1 to C5 alkyl group.

According to another aspect of the present disclosure, there is provided a lithium secondary battery including a positive electrode including a positive electrode active material, a negative electrode including a negative electrode active material, a separator interposed between the negative electrode and the positive electrode, and the non-aqueous electrolyte solution for a lithium secondary battery of the present disclosure.

A non-aqueous electrolyte solution for a lithium secondary battery of the present disclosure includes, as an additive, a Lewis base-based compound represented by Formula 1 including a propargyl group and two nitrogen elements in the molecular structure, so that it is possible to form a stable film on the surface of each of positive and negative electrodes, while at the same time, effectively scavenging by-products generated due to thermal decomposition of lithium salts.

Therefore, since it is possible to prevent the deterioration of the films on the surfaces of the positive and negative electrodes, and effectively suppress the elution of a transition metal from the positive electrode by using the non-aqueous electrolyte solution for a lithium secondary battery of the present disclosure, it is possible to implement a lithium secondary battery in which an increase in initial resistance is suppressed and high-temperature durability is improved.

DETAILED DESCRIPTION OF THE INVENTION

First, before describing the present disclosure, it will be understood that terms or words used in the present specification and claims shall not be construed as being limited to having meanings defined in commonly used dictionaries, but should be interpreted as having meanings and concepts consistent with the technical idea of the present disclosure based on the principle that an inventor may appropriately define concepts of the terms to best explain the disclosure.

Meanwhile, the terms used herein are only used to describe exemplary embodiments, and are not intended to limit the present disclosure. Singular expressions include plural expressions unless the context clearly indicates otherwise.

It will be further understood that the terms "include," "comprise," or "have" when used in the present specification, specify the presence of stated features, numbers, steps, elements, or combinations thereof, but do not preclude the presence or addition of one or more other features, numbers, steps, elements, or combinations thereof.

In the present specification, "%" means wt % unless otherwise noted.

Before describing the present disclosure, it will be understood that in the description of "carbon atoms a to b" herein, "a" and "b" refer to the number of carbon atoms included in a specific functional group. That is, the functional group may include "a" to "b" number of carbon atoms.

In the present specification, the alkyl group may be straight-chain or branched-chain. It may be optionally substituted. In the present specification, unless otherwise defined, "substituted" means that at least one hydrogen bonded to carbon is substituted with an element other than hydrogen, and for example, it means being substituted with an alkyl group having 1 to 5 carbon atoms or a fluorine element.

Hereinafter, the present disclosure will be described in more detail.

In general, a lithium secondary battery may secure high-temperature storage properties as a non-aqueous electrolyte solution is decomposed during an initial charging/discharging and forms a film having a passivation capability on the surfaces of positive and negative electrodes. However, the film may be deteriorated by a Lewis acid material, such as HF and $PF_5$, which is generated due to thermal decomposition of a lithium salt ($LiPF_6$, etc.) widely used in a lithium ion battery. That is, when transition metal elements are eluted from the positive electrode by the attack of the Lewis acid material, there is a change in the structure of the surface, resulting in an increase in the surface resistance of the electrode, and as the metal elements, which are redox centers, are lost, a theoretical capacity may decrease, thereby decreasing an expression capacity. In addition, the eluted transition metal ions as described above are deposited on the negative electrode which reacts in a strong reduction potential band, and consume electrons, and also, destroy the film when deposited, thereby exposing the surface of the negative electrode, and thus, may cause an additional non-aqueous electrolyte solution decomposition reaction. As a result, there is a problem in that the negative electrode resistance and irreversible capacity increase to cause the capacity of a cell to continuously degrade.

Therefore, in order to form a stable film on the surface of an electrode, the present disclosure is to provide a non-aqueous electrolyte solution for a lithium secondary battery including an additive with improved decomposition product scavenging effect and SEI enhancing effect, and a lithium secondary battery including the non-aqueous electrolyte solution.

Non-Aqueous Electrolyte Solution for Lithium Secondary Battery

The present disclosure provides a non-aqueous electrolyte solution for a lithium secondary battery, the non-aqueous electrolyte solution including a lithium salt, an organic solvent, and a compound represented by Formula 1 below.

[Formula 1]

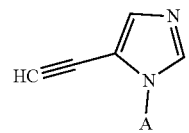

In Formula 1, A is a C1 to C5 alkyl group.

(1) Lithium Salt

First, the lithium salt will be described as follows.

In the non-aqueous electrolyte solution for a lithium secondary battery according to an embodiment of the present disclosure, any lithium salt may be used as the lithium salt without particular limitation as long as it is typically used in an electrolyte solution for a lithium secondary battery, and for example, the lithium salt may include $Li^+$ as a cation, and may include at least one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $B_{10}Cl_{10}^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $CH_3SO_3^-$, $CF_3(CF_2)_7SO_3^-$, $CF_3CO_2^-$, $CH_3CO_2^-$, $SCN^-$, and $(CF_3CF_2SO_2)_2N^-$ as an anion. Specifically, the lithium salt may include at least one selected from the group consisting of LiCl, LiBr, LiI, $LiBF_4$, $LiClO_4$, $LiAlO_4$, $LiAlCl_4$, $LiPF_6$, $LiSbF_6$, $LiAsF_6$, $LiB_{10}Cl_{10}$, LiBOB ($LiB(C_2O_4)_2$), $LiCF_3SO_3$, LiTFSI ($LiN(SO_2CF_3)_2$), LiFSI ($LiN(SO_2F)_2$), $LiCH_3SO_3$, $LiCF_3CO_2$, $LiCH_3CO_2$, and LiBETI ($LiN(SO_2CF_2CF_3)_2$). Specifically, the lithium salt may include a single material selected from the group consisting of $LiBF_4$, $LiClO_4$, $LiPF_6$, LiBOB ($LiB(C_2O_4)_2$), $LiCF_3SO_3$, LiTFSI ($LiN(SO_2CF_3)_2$), LiFSI ($LiN(SO_2F)_2$), and LiBETI ($LiN(SO_2CF_2CF_3)_2$), or a mixture of two or more thereof, and more specifically, may include $LiPF_6$.

The content of the lithium salt may be appropriately changed within a typical range in which a lithium salt may be used, but in order to obtain an optimum effect of forming an anti-corrosive film on the surface of an electrode, the lithium salt may be included in the electrolyte solution at a concentration of 0.8 M to 3.0 M, specifically 1.0 M to 3.0 M.

When the lithium salt is included in the above concentration range, the viscosity of the non-aqueous electrolyte solution may be controlled to implement optimal impregnation, and the mobility of lithium ions may be improved to obtain an effect of improving the capacity properties and cycle properties of a lithium secondary battery.

(2) Organic Solvent

In addition, the organic solvent will be described as follows.

The organic solvent may include a cyclic carbonate-based organic solvent, a linear carbonate-based organic solvent, or a mixed organic solvent thereof.

The cyclic carbonate-based organic solvent is an organic solvent having high viscosity and a high dielectric constant, and thus, is an organic solvent capable of dissociating a lithium salt in an non-aqueous electrolyte solution well, and specific examples thereof may include at least one organic solvent selected from the group consisting of ethylene carbonate (EC), propylene carbonate (PC), 1,2-butylene carbonate, 2,3-butylene carbonate, 1,2-pentylene carbonate, 2,3-pentylene carbonate, and vinylene carbonate, and among them, may include ethylene carbonate.

In addition, the linear carbonate-based organic solvent is an organic solvent having low viscosity and a low dielectric constant, and representative examples thereof may include at least one organic solvent selected from the group consisting of dimethyl carbonate (DMC), diethyl carbonate (DEC), dipropyl carbonate, ethylmethyl carbonate (EMC), methylpropyl carbonate, and ethylpropyl carbonate, and specifically, may include ethylmethyl carbonate (EMC).

In order to prepare an electrolyte solution having a high ion conductivity, it is preferable that a mixture of a cyclic carbonate-based organic solvent and a linear carbonate-based organic solvent is used as the organic solvent. The cyclic carbonate organic solvent and the linear carbonate organic solvent may be mixed at a volume ratio of 1:9 to 5:5, specifically 2:8 to 4:6, and used.

In addition, the organic solvent, if necessary, may further include a linear ester-based organic solvent and/or a cyclic ester-based organic solvent in the cyclic carbonate-based organic solvent and/or the linear carbonate-based organic solvent.

Specific examples of the linear ester-based organic solvent may include at least one organic solvent selected from the group consisting of methyl acetate, ethyl acetate, propyl acetate, methyl propionate, ethyl propionate, propyl propionate, and butyl propionate.

In addition, the cyclic ester-based organic solvent may be at least one organic solvent selected from the group consisting of γ-butyrolactone, γ-valerolactone, γ-caprolactone, σ-valerolactone, and ε-caprolactone.

In addition, the organic solvent may further include at least one organic solvent among an ether-based organic solvent, an amide-based organic solvent, and a nitrile-based organic solvent.

As the ether-based organic solvent, any one selected from the group consisting of dimethyl ether, diethyl ether, dipropyl ether, methyl ethyl ether, methyl propyl ether, and ethyl propyl ether, or a mixture of two or more thereof may be used.

The nitrile-based solvent may be at least one selected from the group consisting of acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

(3) Electrolyte Solution Additive

The non-aqueous electrolyte solution for a lithium secondary battery of the present disclosure includes the compound represented by Formula 1 below as an electrolyte solution additive.

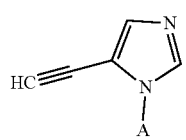

[Formula 1]

In Formula 1, A is a C1 to C5 alkyl group.

Specifically, in Formula 1 above, A is a C1 to C4 alkyl group, and more specifically, in Formula 1 above, A may be C1 to C3 alkyl group.

Preferably, the compound represented by Formula 1 above may be a compound represented by Formula 1a below.

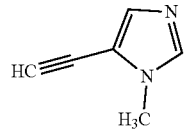

[Formula 1a]

The compound represented by Formula 1 is a compound including an imidazole group containing two nitrogen elements and a propargyl group together in the molecular structure, wherein the two nitrogen elements may act as a Lewis base to increase the binding force with a Lewis acid material generated as a decomposition product of a lithium salt. As a result, by-products causing a secondary battery to deteriorate at high temperatures, for example, the by-products generated due to thermal decomposition of the lithium salt may be easily scavenged. In addition, a nitrogen (N) atom-based material may be electrochemically reduced and decomposed to form a nitrogen (N) atom-based film SEI on the surface of a negative electrode. The nitrogen (N) atom-based film has properties of being maintained without being easily decomposed when the battery is exposed to high-temperatures. Therefore, by imparting properties in which the SEI film is stably maintained without being decomposed on the negative electrode, the compound represented by Formula 1 above may control an additional negative electrode reduction reaction of a transition metal caused by SEI decomposition, and prevent the transition metal eluted during high-temperature storage from being deposited on the negative electrode.

In addition, the compound represented by Formula 1 above includes a propargyl group having a triple bond, which is known to have a metal ion adsorption capacity, in the molecular structure, and thus, may be easily adsorbed with a metal foreign matter such as Fe, Co, Mn, or Ni eluted from a positive electrode during charging/discharging, a metal foreign matter such as Cu eluted from the negative electrode, or a metal foreign matter mixed in raw materials or during a manufacturing process. As a result, since it is possible to suppress the eluted metal foreign matter from growing into a dendrite in the negative electrode, it is possible to suppress an abnormal voltage drop phenomenon during high-temperature storage caused by the eluted metal foreign matter. In addition, when a predetermined voltage is reached during a charging/discharging process, the propargyl group is reduced on the surface of the negative electrode and forms a stable ion conductive film, so that an additional electrolyte decomposition reaction may be suppressed, and furthermore, even during overcharging or high-temperature storage, occlusion and release of lithium ions from the negative electrode are facilitated, so that the abnormal voltage drop phenomenon of a secondary battery may be suppressed, and cycle lifespan properties and high-temperature storage performance thereof may be improved.

In the case of the non-aqueous electrolyte solution for a lithium secondary battery of the present disclosure including the compound of Formula 1 as an additive, a more robust passivation film may be formed on the surfaces of positive and negative electrodes, and accordingly, the deterioration of the passivation film at high temperatures may be prevented, so that a lithium secondary battery with improved high-temperature durability may be implemented.

Meanwhile, the compound represented by Formula 1 above may be included in an amount of 0.5 wt % to 6.0 wt % based on the total weight of the non-aqueous electrolyte solution for a lithium secondary battery.

When the compound represented by Formula 1 above is included in the above range, it is possible to form a robust film on the surface of a positive electrode while suppressing disadvantages, such as side reactions caused by an additive, a capacity decrease, and a resistance increase caused by an additive, to the maximum, thereby effectively suppressing the elution of transition metals of a positive electrode active material at high temperatures, and to effectively scavenge thermal decomposition products of a lithium salt, so that a lithium secondary battery having excellent high-temperature durability may be implemented.

That is, when the content of the electrolyte solution additive for a secondary battery is 0.5 wt % or greater, it is possible to more stably maintain the effect of scavenging thermal decomposition products of a lithium salt such as HF or $PF_5$ and the effect of suppressing the transition metal elution by protecting the positive electrode during the driving of the battery. In addition, when the content of the compound represented by Formula 1 above is 6.0 wt % or less, it is possible to control the viscosity of the non-aqueous electrolyte solution to implement optimal impregnation, to effectively suppress an increase in electrode resistance due to the decomposition of the additive, and to further increase ion conductivity in the battery, thereby preventing degradation in rate properties or low-temperature lifespan properties during high-temperature storage.

Specifically, the compound represented by Formula 1 above may be included in an amount of 0.5 wt % to 5.0 wt %, specifically 0.5 wt % to 3.0 wt %, preferably 0.5 wt % to 1.0 wt %, based on the total weight of the non-aqueous electrolyte solution for a lithium secondary battery.

(4) Other Additives

Meanwhile, the non-aqueous electrolyte solution of the present disclosure may further include, if necessary, other additional additives in addition to the compound represented by Formula 1 above to prevent the non-aqueous electrolyte solution from being decomposed in a high-output environment and causing a negative electrode to collapse, or to further improve low-temperature high-rate discharge properties, high-temperature stability, overcharge prevention, the effect of suppressing battery expansion at high temperatures, and the like.

Examples of the additive may include at least one selected from the group consisting of a cyclic carbonate-based compound, a halogen-substituted carbonate-based compound, a sultone-based compound, a sulfate-based compound, a phosphate-based or phosphite-based compound, a borate-based compound, a nitrile-based compound, a benzene-based compound, an amine-based compound, a silane-based compound, and a lithium salt-based compound.

The cyclic carbonate-based compound may be, for example, vinylene carbonate (VC), vinylethylene carbonate, or the like.

The halogen-substituted carbonate-based compound may be, for example, fluoroethylene carbonate (FEC) and the like.

The sultone-based compound may be, for example, at least one compound selected from the group consisting of 1,3-propane sultone (PS), 1,4-butane sultone, ethene sulfone, 1,3-propene sultone (PRS), 1,4-butene sultone, and 1-methyl-1,3-propene sultone.

The sulfate-based compound may be, for example, ethylene sulfate (ESa), trimethylene sulfate (TMS), methyl trimethylene sulfate (MTMS), or the like.

The phosphate-based or phosphite-based compound may be, for example, one or more compounds selected from the group consisting of lithium difluoro(bisoxalato)phosphate, lithium difluorophosphate, tris(trimethylsilyl) phosphate, tris(trimethylsilyl) phosphite, tris(2,2,2-trifluoroethyl) phosphate, and tris(trifluoroethyl) phosphite.

The borate-based compound may be tetraphenylborate, lithium oxalyldifluoroborate (LiODFB), lithium bisoxalatoborate ($LiB(C_2O_4)_2$, LiBOB), or the like.

The nitrile-based compound may be, for example, at least one compound selected from the group consisting of succinonitrile, adiponitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

The benzene-based compound may be, for example, fluorobenzene or the like, the amine-based compound may be triethanolamine, ethylenediamine, or the like, and the silane-based compound may be tetravinylsilane or the like.

The lithium salt-based compound is a compound different from the lithium salt included in the non-aqueous electrolyte solution, and may be $LiPO_2F_2$, $LiBF_4$, or the like.

Among the additional additives, when vinylene carbonate, vinylethylene carbonate, or succinonitrile is included, it is possible to form a more robust SEI film on the surface of a negative electrode during an initial activation process of a secondary battery. In addition, when $LiBF_4$ is included, it is possible to suppress the generation of a gas which may be generated due to the decomposition of an electrolyte solution during high-temperature storage, thereby improving high-temperature stability of a secondary battery.

The other additive may be used in combination of two or more compounds, and the total content of the compound represented by Formula 1 above and the other additive may be 50 wt % or less, specifically 0.05 to 20 wt %, more specifically 0.05 to 10 wt %, based on the total weight of the non-aqueous electrolyte solution. When the total content of the additives satisfy the above range, it is possible to improve low-temperature output properties of a battery, to further effectively improve high-temperature storage properties and high-temperature lifespan properties thereof, and to prevent side reactions of the battery caused by the additives remaining after a reaction.

Lithium Secondary Battery

In addition, another embodiment of the present disclosure provides a lithium secondary battery including the non-aqueous electrolyte solution for a lithium secondary battery of the present disclosure.

Specifically, the lithium secondary battery may include a positive electrode, a negative electrode, and the above-described non-aqueous electrolyte solution for a lithium secondary battery. More specifically, the lithium secondary battery may include a positive electrode, a negative electrode, a separator interposed between the positive electrode and the negative electrode, and the above-described non-aqueous electrolyte solution for a lithium secondary battery.

Meanwhile, the lithium secondary battery of the present disclosure may be manufactured by forming an electrode assembly in which a positive electrode, a separator, and a negative electrode are sequentially stacked, accommodating the electrode assembly in a battery case, and then introducing the non-aqueous electrolyte solution of the present disclosure to the battery case.

A typical method for manufacturing a lithium secondary battery known in the art may be applied to the method for manufacturing the lithium secondary battery of the present disclosure, which will be described in detail below.

(1) Positive Electrode

The positive electrode according to the present disclosure may include a positive electrode active material layer including a positive electrode active material, and if necessary, the positive electrode active material layer may further include a conductive material and/or a binder.

The positive electrode active material is a compound capable of reversible intercalation and de-intercalation of lithium, and may include a lithium transition metal oxide including one or more metals selected from cobalt, manganese, nickel, or aluminum, and lithium, and specifically, may include at least one of a lithium-manganese-based oxide, a lithium iron phosphate, or a lithium-nickel-manganese-cobalt-based oxide (e.g., $Li(Ni_pCo_qMn_{r1})O_2$ (wherein, 0<p<1, 0<q<1, 0<r1<1, p+q+r1=1)) which have high capacity properties and safety of a battery. Specifically, the positive electrode may include at least one of a lithium iron phosphate, or a lithium-nickel-manganese-cobalt-based oxide.

Specifically, the lithium-manganese-based oxide may be $LiMnO_2$ or $LiMn_2O_4$, and the lithium iron phosphate may be, for example, $LiFePO_4$.

In addition, the lithium-nickel-manganese-cobalt-based oxide may include at least one of $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, or $Li(Ni_{0.8}Mn_{0.1}Co_{0.1})O_2$, and among them, it is preferable that a lithium transition metal oxide having a nickel content of 60 atm % or greater in the transition metal is included. That is, since the higher the nickel content in the transition metal, the higher the capacity to be implemented, it is more advantageous in implementing a high capacity to use a lithium transition metal oxide having a nickel content of 60 atm % or greater. The lithium composite metal oxide as described above may be at least one selected from the group consisting of Li ($Ni_{0.6}Mn_{0.2}Co_{0.2})O_2$, $Li(Ni_{0.7}Mn_{0.15}Co_{0.15})O_2$, and $Li(Ni_{0.8}Mn_{0.1}Co_{0.1})O_2$.

Meanwhile, in addition to the lithium transition metal oxide, the positive electrode active material of the present disclosure may further comprises at least one of a lithium-cobalt-based oxide (e.g., $LiCoO_2$, etc.), a lithium-nickel-based oxide (e.g., $LiNiO_2$, etc.), a lithium-nickel-manganese-based oxide (e.g., $LiNi_{1-Y}Mn_YO_2$ (0<Y<1) and $LiMn_{2-z}Ni_zO_4$ (0<Z<2)), a lithium-nickel-cobalt-based oxide (e.g., $LiNi_{1-Y1}Co_{Y1}O_2$ (0<Y1<1)), a lithium-manganese-cobalt-based oxide (e.g., $LiCo_{1-Y2}Mn_{Y2}O_2$ (0<Y2<1) and $LiMn_{2-z1}Co_{z1}O_4$ (0<Z1<2)), a lithium-nickel-manganese-cobalt-based oxide (e.g., $Li(Ni_{p1}CO_{q1}Mn_{r2})O_4$ (0<p1<2, 0<q1<2, 0<r2<2, p1+q1+r2=2)), a lithium-nickel-cobalt-transition metal (M) oxide (e.g., $Li(Ni_{p2}Co_{q2}Mn_{r3}M_{s2})O_2$ (wherein M is selected from the group consisting of Al, Fe, V, Cr, Ti, Ta, Mg, and Mo, and p2, q2, r3, and s2 are each an atomic fraction of stand-alone elements, wherein 0<p2<1, 0<q2<1, 0<r3<1, 0<s2<1, p2+q2+r3+s2=1)), or the like, and any one thereof or a compound of two or more thereof may be included.

The positive electrode active material may be included in an amount of 90 wt % to 99 wt %, specifically 93 wt % to 98 wt %, based on the total weight of solids in the positive electrode active material layer.

The conductive material is not particularly limited as long as it has conductivity without causing a chemical change in the battery, and for example, carbon powder such as carbon black, acetylene black, Ketjen black, channel black, furnace black, lamp black, or thermal black; graphite powder of natural graphite, artificial graphite, graphite, or the like, which has a very developed crystal structure; conductive fiber such as carbon fiber or metal fiber; conductive powder such as fluorocarbon powder, aluminum powder, or nickel powder; a conductive whisker such as zinc oxide and potassium titanate; a conductive metal oxide such as titanium oxide; a conductive material such as a polyphenylene derivative, and the like may be used.

The conductive material is typically added in an amount of 1 to 30 wt % based on the total weight of solids in the positive electrode active material layer.

The binder is a component serving to improve bonding between positive electrode active material particles and adhesion between the positive electrode active material and a current collector, and is typically added in an amount of 1 to 30 wt % based on the total weight of solids in the positive electrode active material layer. Examples of the binder may include a fluorine resin-based binder including polyvinylidene fluoride (PVDF) and polytetrafluoroethylene (PTFE); a rubber-based binder including styrene-butadiene rubber (SBR), acrylonitrile-butadiene rubber, and styrene-isoprene rubber; a cellulose-based binder including carboxyl methyl cellulose (CMC), starch, hydroxypropyl cellulose, and regenerated cellulose; a polyvinyl alcohol-based binder including polyvinyl alcohol; a polyolefin-based binder including polyethylene and polypropylene; a polyimide-based binder; a polyester-based binder; a silane-based binder, and the like.

The positive electrode of the present disclosure as described above may be manufactured by a method for manufacturing a positive electrode known in the art. For example, the positive electrode may be manufactured by a method of preparing a positive electrode slurry by dissolving or dispersing a positive electrode active material, a binder and/or a conductive material in a solvent and applying the positive electrode slurry on a positive electrode current collector, followed by drying and roll-pressing to form a positive electrode active material layer, a method of casting the positive electrode active material layer on a separate support, and then laminating a film obtained by peeling off the support on a positive electrode current collector, or the like.

The positive electrode current collector is not particularly limited as long as it has conductivity without causing a chemical change in the battery. For example, stainless steel, aluminum, nickel, titanium, fired carbon, or aluminum or stainless steel that is surface-treated with one of carbon, nickel, titanium, silver, and the like may be used.

The solvent may include an organic solvent such as N-methyl-2-pyrrolidone (NMP), and may be used in an amount such that a preferred viscosity is achieved when the positive electrode active material and optionally, a binder and a conductive material, and the like are included. For example, the solvent may be included in an amount such that the concentration of solids in the active material slurry including the positive electrode active material, and optionally, a binder and a conductive material is 10 wt % to 70 wt %, preferably 20 wt % to 60 wt %.

(2) Negative Electrode

Next, the negative electrode will be described.

The negative electrode according to the present disclosure includes a negative electrode active material layer including a negative electrode active material, and the negative electrode active material layer may include, if necessary, a conductive material and/or a binder.

As the negative electrode active material, various negative electrode active materials used in the art, for example, a carbon-based negative electrode active material, a silicon-based negative electrode active material, or a mixture thereof may be used.

According to an embodiment, the negative electrode active material may include a carbon-based negative electrode active material, and, as the carbon-based negative electrode active material, various carbon-based negative electrode active materials used in the art, for example, a graphite-based materials such as natural graphite, artificial graphite, and Kish graphite; pyrolytic carbon, mesophase pitch based carbon fiber, meso-carbon microbeads, mesophase pitches, high-temperature sintered carbon such as petroleum or coal tar pitch derived cokes, soft carbon, and hard carbon may be used. A shape of the carbon-based negative electrode active material is not particularly limited, and materials of various shapes, such as an irregular shape, planar shape, flaky shape, spherical shape, or fibrous shape, may be used.

Preferably, the carbon-based negative electrode active material may include at least one of natural graphite and artificial graphite. More preferably, the carbon-based negative electrode active material may include natural graphite and artificial graphite. In a case in which the natural graphite and the artificial graphite are used together, adhesion with the current collector may be increased to suppress exfoliation of the active material.

According to another embodiment, the negative electrode active material may include a silicon-based negative electrode active material, and the silicon-based negative electrode active material, for example, may include at least one selected from the group consisting of metallic silicon (Si), silicon oxide ($SiO_x$, where $0<x\leq2$), silicon carbide (SiC), and a Si—Y alloy (where Y is an element selected from the group consisting of alkali metal, alkaline earth metal, a Group 13 element, a Group 14 element, transition metal, a rare earth element, and a combination thereof, and is not Si). The element Y may be selected from the group consisting of Mg, Ca, Sr, barium (Ba), radium (Ra), Sc, Y, Ti, Zr, hafnium (Hf), rutherfordium (Rf), V, Nb, Ta, dubnium (Db), Cr, Mo, W, seaborgium (Sg), technetium (Tc), rhenium (Re), bohrium (Bh), Fe, lead (Pb), ruthenium (Ru), osmium (Os), hassium (Hs), rhodium (Rh), iridium (Ir), palladium (Pd), platinum (Pt), Cu, silver (Ag), gold (Au), Zn, cadmium (Cd), B, Al, Ga, tin (Sn), In, Ti, germanium (Ge), phosphorus (P), arsenic (As), antimony (Sb), bismuth (Bi), sulfur (S), selenium (Se), tellurium (Te), polonium (Po), and a combination thereof.

Since the silicon-based negative electrode active material has higher capacity characteristics than the carbon-based negative electrode active material, better capacity characteristics may be obtained when the silicon-based negative electrode active material is further included. However, with respect to a negative electrode including the silicon-based negative electrode active material, it contains more 0-rich components in the SEI than a graphite negative electrode, and the SEI containing the 0-rich components tends to be more easily decomposed when a Lewis acid, such as HF or $PF_5$, is present in the electrolyte. Thus, with respect to the negative electrode including the silicon-based negative electrode active material, there is a need to suppress the formation of the Lewis acid, such as HF and $PF_5$, or remove (or scavenge) the formed Lewis acid in order to stably maintain the SEI. The non-aqueous electrolyte according to the present invention includes the compound acting as a Lewis base, thereby suppressing generation of Lewis acid to suppress dissolution of transition metal from the cathode and effectively prevent damage to the SEI formed on the surface of the silicon-based anode active material.

According to another embodiment, the negative electrode active material may include a mixture of a carbon-based negative electrode active material and a silicon-based negative electrode active material.

Specific examples of the carbon-based negative electrode active material and the silicon-based negative electrode active material are the same as described above.

A mixing ratio of the silicon-based negative electrode active material to the carbon-based negative electrode active material may be in a range of 3:97 to 99:1, preferably 5:95 to 30:70, and more preferably 5:95 to 15:85, as a weight ratio. In a case in which the mixing ratio of the silicon-based negative electrode active material to the carbon-based negative electrode active material satisfies the above range, since a volume expansion of the silicon-based negative electrode active material is suppressed while capacity characteristics are improved, excellent cycle performance may be secured.

The negative electrode active material may be included in an amount of 80 wt % to 99 wt % based on the total weight of solids in the negative electrode active material layer. In a case in which the amount of the negative electrode active material satisfies the above range, excellent capacity characteristics and electrochemical properties may be obtained.

The conductive material is a component for further improving the conductivity of the negative electrode active material, and may be added in an amount of 1 to 20 wt % based on the total weight of solids in the negative electrode active material layer. The conductive material is not particularly limited as long as it has conductivity without causing a chemical change in the battery, and for example, graphite such as natural graphite or artificial graphite; carbon black such as acetylene black, Ketjen black, channel black, furnace black, lamp black, and thermal black; conductive fiber such as carbon fiber and metal fiber; conductive powder such as fluorocarbon powder, aluminum powder, and nickel powder; a conductive whisker such as zinc oxide and potassium titanate; a conductive metal oxide such as titanium oxide; a conductive material such as a polyphenylene derivative, and the like may be used.

The binder is a component for assisting in binding between a conductive material, an active material, and a current collector, and is typically added in an amount of 1 to 30 wt % based on the total weight of solids in a negative electrode active material layer. Examples of the binder may include a fluorine resin-based binder including polyvinylidene fluoride (PVDF) or polytetrafluoroethylene (PTFE); a rubber-based binder including styrene-butadiene rubber (SBR), acrylonitrile-butadiene rubber, and styrene-isoprene rubber; a cellulose-based binder including carboxyl methyl cellulose (CMC), starch, hydroxypropyl cellulose, and regenerated cellulose; a polyvinyl alcohol-based binder including polyvinyl alcohol; a polyolefin-based binder including polyethylene and polypropylene; a polyimide-based binder; a polyester-based binder; a silane-based binder, and the like.

The negative electrode may be manufactured by a method for manufacturing a negative electrode known in the art. For example, the negative electrode may be manufactured by preparing a negative electrode slurry by dissolving or dispersing a negative electrode active material, and optionally, a binder and a conductive material in a solvent and applying the negative electrode slurry on a negative electrode current collector, followed by roll-pressing and drying to form a negative electrode active material layer, or by casting the negative electrode active material layer on a separate support, and then laminating a film obtained by peeling off the support on a negative electrode current collector.

The negative electrode current collector typically has a thickness of 3 to 500 μm. The negative electrode current collector is not particularly limited as long as it has high conductivity without causing a chemical change in the battery, and for example, copper, stainless steel, aluminum, nickel, titanium, fired carbon, copper or stainless steel that is surface-treated with one of carbon, nickel, titanium, silver, and the like, an aluminum-cadmium alloy, and the like may be used. Also, as in the case of the positive electrode current collector, microscopic irregularities may be formed on the surface of the negative electrode current collector to improve the biding force of a negative electrode active material, and the negative electrode current collector may be used in various forms of such as a film, a sheet, a foil, a net, a porous body, a foam body, and a non-woven fabric body.

The solvent may include water or an organic solvent such as NMP, an alcohol, or the like, and may be used in an amount such that a preferred viscosity is achieved when the negative electrode active material, and optionally, a binder, a conductive material, and the like are included. For example, the solvent may be included in an amount such that the concentration of solids in the active material slurry including the negative electrode active material, and optionally, a binder and a conductive material is 50 wt % to 75 wt %, preferably 50 wt % to 65 wt %.

(3) Separator

The lithium secondary battery according to the present disclosure includes a separator between the positive electrode and the negative electrode.

The separator is to separate the negative electrode and the positive electrode and to provide a movement path for lithium ions, and any separator may be used without particular limitation as long as it is a separator commonly used in a lithium secondary battery, but a separator having low resistance to ion movement in an electrolyte, thereby having excellent electrolyte moisture-retention is particularly preferable.

Specifically, as the separator, a porous polymer film, for example, a porous polymer film manufactured using a polyolefin-based polymer such as an ethylene homopolymer, a propylene homopolymer, an ethylene/butene copolymer, an ethylene/hexene copolymer, and an ethylene/methacrylate copolymer, or a stacked structure having two or more layers thereof may be used. Also, a typical porous non-woven fabric, for example, a non-woven fabric formed of glass fiber having a high melting point, polyethylene terephthalate fiber, or the like may be used. Furthermore, a coated separator including a ceramic component or a polymer material may be used to secure heat resistance or mechanical strength, and may optionally be used in a single-layered or multi-layered structure.

The lithium secondary battery according to the present disclosure as described above may be usefully used in portable devices such as mobile phones, laptop computers, and digital cameras, in electric cars such as a hybrid electric vehicle (HEV), and the like.

Accordingly, according to another embodiment of the present disclosure, a battery module including the lithium secondary battery as a unit cell, and a battery pack including the battery module are provided.

The battery module or the battery pack may be used as a power source of one or more medium-and-large-sized devices such as a power tool, an electric car such as an electric vehicle (EV), a hybrid electric vehicle (HEV), and a plug-in hybrid electric vehicle (PHEV), and a power storage system.

The external shape of the lithium secondary battery of the present disclosure is not particularly limited, but may be a cylindrical shape using a can, a square shape, a pouch shape, a coin shape, or the like.

The lithium secondary battery according to the present disclosure may be used in a battery cell which is used as a power source for a small-sized device, and may also be preferably used as a unit cell for a medium- and large-sized battery module including a plurality of battery cells.

Hereinafter, the present disclosure will be described in detail with reference to examples.

At this time, the examples according to the present disclosure may be modified into other various forms, and the scope of the present disclosure should not be construed as being limited to the examples described below. The examples of the present disclosure are provided to describe the present disclosure more fully to those skilled in the art.

Hereinafter, the present disclosure will be described in detail with reference to specific examples.

EXAMPLES

Example 1

(Preparation of Non-Aqueous Electrolyte Solution)

In 99.0 g of a non-aqueous organic solvent in which ethylene carbonate (EC) and ethylmethyl carbonate (EMC) were mixed in a volume ratio of 30:70, $LiPF_6$ was dissolved to 1.0 M, and then 0.5 g of a compound represented by Formula 1a and 0.5 g of vinylene carbonate (VC) were added thereto to prepare a non-aqueous electrolyte solution.

(Manufacturing of Secondary Battery)

A positive electrode active material ($Li(Ni_{0.8}Co_{0.1}Mn_{0.1})O_2$; NMC811), carbon black as a conductive material, and polyvinylidene fluoride as a binder were added in a weight ratio of 97.5:1:1.5 to N-methyl-2-pyrrolidone (NMP), which was a solvent, to prepare a positive electrode slurry (solid content 50 wt %). The positive electrode slurry was applied and dried on a positive electrode current collector (an Al thin film) having a thickness of 15 μm, and then roll-pressed to manufacture a positive electrode.

A negative electrode active material (weight ratio of graphite:SiO=95:5), a binder (SBR-CMC), and a conductive material (carbon black) were added in a weight ratio of 95:3.5:1.5 to water, which was a solvent, to prepare a negative electrode slurry (solid content 60 wt %). The negative electrode slurry was applied and dried on a copper (Cu) thin film, which was a negative electrode current collector, having a thickness of 6 μm, and then roll-pressed to manufacture a negative electrode.

The positive electrode, a polyolefin-based porous separator on which inorganic particles ($Al_2O_3$) were applied, and the negative electrode were sequentially stacked to manufacture an electrode assembly.

The assembled electrode assembly was accommodated in a battery case, and 6 mL of the prepared non-aqueous electrolyte solution was injected thereto to manufacture a stack cell (capacity: 2 Ah).

Example 2

A lithium secondary battery was manufactured in the same manner as in Example 1 except that $LiPF_6$ was dissolved to 1.0 M in 98.5 g of the non-aqueous organic solvent, and then 1.0 g of the compound represented by Formula 1a and 0.5 g of vinylene carbonate were added thereto to prepare a non-aqueous electrolyte solution (see Table 1 below).

Example 3

A lithium secondary battery was manufactured in the same manner as in Example 1 except that $LiPF_6$ was dissolved to 1.0 M in 96.5 g of the non-aqueous organic solvent, and then 3.0 g of the compound represented by Formula 1a and 0.5 g of vinylene carbonate were added thereto to prepare a non-aqueous electrolyte solution (see Table 1 below).

Example 4

A lithium secondary battery was manufactured in the same manner as in Example 1 except that $LiPF_6$ was dissolved to 1.0 M in 94.5 g of the non-aqueous organic solvent, and then 5.0 g of the compound represented by Formula 1a and 0.5 g of vinylene carbonate were added thereto to prepare a non-aqueous electrolyte solution (see Table 1 below).

Example 5

A lithium secondary battery was manufactured in the same manner as in Example 1 except that $LiPF_6$ was dissolved to 1.0 M in 93.5 g of the non-aqueous organic solvent, and then 6.0 g of the compound represented by Formula 1a and 0.5 g of vinylene carbonate were added thereto to prepare a non-aqueous electrolyte solution (see Table 1 below).

Comparative Example 1

A lithium secondary battery was manufactured in the same manner as in Example 1 except that $LiPF_6$ was dissolved to 1.0 M in 97.0 g of the non-aqueous organic solvent, and then only 3.0 g of vinylene carbonate was added as an additive thereto to prepare a non-aqueous electrolyte solution (see Table 1 below).

Comparative Example 2

A lithium secondary battery was manufactured in the same manner as in Example 1 except that $LiPF_6$ was dissolved to 1.0 M in 96.5 g of the non-aqueous organic solvent, and then 3.0 g of a compound represented by Formula 2 below and 0.5 g of vinylene carbonate were added thereto to prepare a non-aqueous electrolyte solution (see Table 1 below).

[Formula 2]

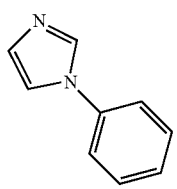

Comparative Example 3

A lithium secondary battery was manufactured in the same manner as in Example 1 except that $LiPF_6$ was dissolved to 1.0 M in 96.5 g of the non-aqueous organic solvent, and then 3.0 g of a compound represented by Formula 3 below and 0.5 g of vinylene carbonate were added thereto to prepare a non-aqueous electrolyte solution (see Table 1 below).

[Formula 3]

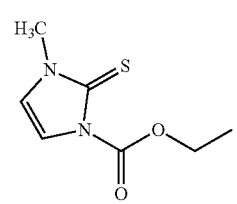

TABLE 1

| | Non-aqueous organic solvent content (g) | Additive Formula | Addition amount (g) | Other additives Type | Addition amount (g) |
|---|---|---|---|---|---|
| Example 1 | 99.0 | 1a | 0.5 | VC | 0.5 |
| Example 2 | 98.5 | 1a | 1.0 | VC | 0.5 |
| Example 3 | 96.5 | 1a | 3.0 | VC | 0.5 |
| Example 4 | 94.5 | 1a | 5.0 | VC | 0.5 |
| Example 5 | 93.5 | 1a | 6.0 | VC | 0.5 |
| Comparative Example 1 | 97.0 | — | — | VC | 3.0 |
| Comparative Example 2 | 96.5 | 2 | 3.0 | VC | 0.5 |
| Comparative Example 3 | 96.5 | 3 | 3.0 | VC | 0.5 |

In Table 1 above, VC is abbreviation for vinylene carbonate.

EXPERIMENTAL EXAMPLES

Experimental Example 1: Evaluation of Initial Resistance

The lithium secondary batteries manufactured in Examples 1 to 5 and the lithium secondary batteries manufactured in Comparative Examples 1 to 3 were each charged to 4.2 V at room temperature (25° C.) at a 0.33 C rate under a constant current/constant voltage condition, discharged to 50% of depth of discharge (DOD) to meet SOC 50%, and then discharged for 10 seconds under the condition of 2.5 C rate to measure the initial resistance thereof using a PNE-0506 charger/discharger (Manufacturer: PNE solution). The results are shown in Table 2 below.

TABLE 2

| | Initial resistance (mohm) |
|---|---|
| Example 1 | 5.23 |
| Example 2 | 5.31 |
| Example 3 | 5.65 |
| Example 4 | 5.89 |
| Example 5 | 7.54 |

TABLE 2-continued

|  | Initial resistance (mohm) |
|---|---|
| Comparative Example 1 | 8.56 |
| Comparative Example 2 | 10.35 |
| Comparative Example 3 | 11.98 |

Referring to Table 2 above, it can be seen that the initial resistance of each of the secondary batteries of Examples 1 to 5 of the present disclosure is about 7.54 mohm or less.

Meanwhile, it can be seen that the initial resistance of each of the secondary battery of Comparative Example 1 not including the electrolyte solution additive of the present disclosure, the secondary battery of Comparative Example 2 including the compound represented by Formula 2, and the secondary battery of Comparative Example 3 including the compound represented by Formula 3 were all increased compared to that of each of the secondary batteries of Examples 1 to 5.

Experimental Example 2: Evaluation of Capacity Retention Rate and Resistance Increase Rate at High Temperature (45° C.)

The lithium secondary batteries manufactured in Examples 1 to 5 and the lithium secondary batteries manufactured in Comparative Examples 1 to 3 were each charged to 4.2 V at 45° C. at a 0.33 C rate under a constant current/constant voltage condition, and then discharged to 3 V at a 0.33 C rate under a constant current/constant voltage condition, which was set to one cycle, and then 200 cycles of the charging/discharging were performed to measure the capacity retention rate (%) and resistance increase rate (%). The capacity retention rate (%) was calculated according to Equation 1 below, and the resistance increase rate (%) was calculated according to Equation 2 below. The measurement results are shown in Table 3 below.

Capacity retention rate (%)=(discharge capacity after 200 cycles/discharge capacity after 1 cycle)× 100  [Equation 1]

Resistance increase rate (%)={(resistance after 200 cycles−resistance after 1 cycle)/resistance after 1 cycle}×100  [Equation 2]

TABLE 3

|  | Capacity retention rate (%) after 200 cycles | Resistance increase rate (%) after 200 cycles |
|---|---|---|
| Example 1 | 92.40 | 5.34 |
| Example 2 | 92.82 | 5.22 |
| Example 3 | 93.55 | 4.54 |
| Example 4 | 93.61 | 4.11 |
| Example 5 | 93.82 | 4.07 |
| Comparative Example 1 | 81.20 | 17.90 |
| Comparative Example 2 | 83.24 | 15.65 |
| Comparative Example 3 | 83.18 | 14.98 |

Referring to Table 3 above, it can be seen that the capacity retention rate (%) of each of the secondary batteries of Examples 1 to 5 of the present disclosure after the 200 cycles was about 92.40% or greater, and the resistance increase rate (%) thereof was about 5.34% or less. That is, it can be seen that as the content of the additive increased, the capacity retention rate improved and the resistance increase rate decreased. This phenomenon seems to occur because as the content of the additive increases, the amount of residual additive remaining after being consumed in an initial stage increases, and the residual additive is used for regenerating SEI which collapses as the cycle progresses, thereby suppressing additional decomposition reactions, resulting in the improvement in capacity retention rate and increase in resistance increase rate.

However, as shown in Table 2 of Experimental Example 1, in the case of the secondary battery of Experimental Example 5 including a slightly large amount of the additive, there is a disadvantage in that the film resistance increases in an initial stage, so that the initial resistance is high. Therefore, considering the result of the initial resistance of the secondary battery, it seems that there is a need to control the additive content range, properly.

Meanwhile, it can be seen that the capacity retention rate (%) and the resistance increase rate (%) after the 200 cycles of each of the secondary battery of Comparative Example 1 not including the electrolyte solution additive of the present disclosure, the secondary battery of Comparative Example 2 including the compound represented by Formula 2, and the secondary battery of Comparative Example 3 including the compound represented by Formula 3 were all deteriorated compared to those of each of the secondary batteries of Examples 1 to 5.

Experimental Example 3. Evaluation of Volume Increase Rate after High-Temperature Storage The lithium secondary batteries manufactured in Examples 1 to 5 and the lithium secondary batteries manufactured in Comparative Examples 1 to 3 were each charged to 4.2 V at room temperature (25° C.) at a 0.33 C rate under a constant current/constant voltage condition, discharged to 50% of depth of discharge (DOD) to meet SOC 50%, and then discharged for 10 seconds under the condition of 2.5 C rate to measure the initial thickness.

Thereafter, each lithium secondary battery was stored for two weeks at 60° C., and then the thickness thereof after the high-temperature storage was measured, and the results are shown in Table 4 below.

TABLE 4

|  | Volume increase rate (%) |
|---|---|
| Example 1 | 10.47 |
| Example 2 | 9.57 |
| Example 3 | 8.54 |
| Example 4 | 7.21 |
| Example 5 | 7.02 |
| Comparative Example 1 | 23.20 |
| Comparative Example 2 | 21.46 |
| Comparative Example 3 | 20.23 |

Referring to Table 4 above, it can be seen that the volume increase rate (%) after high-temperature storage of each of the secondary batteries of Examples 1 to 5 of the present disclosure is improved compared to that of each of the secondary batteries of Comparative Examples 1 to 3.

What is claimed is:
1. A lithium secondary battery comprising:
a positive electrode comprising a positive electrode active material;
a negative electrode comprising a negative electrode active material;
a separator interposed between the negative electrode and the positive electrode; and a non-aqueous electrolyte solution comprising:
a lithium salt;
an organic solvent; and
a compound represented by Formula 1:

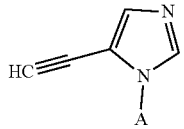

[Formula 1]

wherein in Formula 1,
A is a C1 to C5 alkyl group.

2. The lithium secondary battery of claim 1, wherein in Formula 1, A is a C1 to C4 alkyl group.

3. The lithium secondary battery of claim 2, wherein in Formula 1, A is a C1 to C3 alkyl group.

4. The lithium secondary battery of claim 1, wherein the compound represented by Formula 1 is a compound represented by Formula 1a:

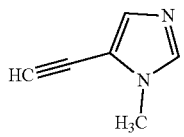

[Formula 1a]

5. The lithium secondary battery of claim 1, wherein the compound represented by Formula 1 is included in an amount of 0.5 wt % to 6.0 wt % based on the total weight of the non-aqueous electrolyte solution.

6. The lithium secondary battery of claim 5, wherein the compound represented by Formula 1 is included in an amount of 0.5 wt % to 5.0 wt % based on the total weight of the non-aqueous electrolyte solution.

7. The lithium secondary battery of claim 1, wherein the lithium salt comprises at least one selected from the group consisting of $LiBF_4$, $LiClO_4$, $LiAlO_4$, $LiAlCl_4$, $LiPF_6$, $LiSbF_6$, $LiAsF_6$, $LiB_{10}Cl_{10}$, LiBOB ($LiB(C_2O_4)_2$), $LiCF_3SO_3$, LiTFSI ($LiN(SO_2CF_3)_2$), LiFSI($LiN(SO_2F)_2$), $LiCH_3SO_3$, $LiCF_3CO_2$, $LiCH_3CO_2$, and LiBETI ($LiN(SO_2CF_2CF_3)_2$).

8. The lithium secondary battery of claim 1, wherein the organic solvent comprises a cyclic carbonate-based organic solvent, a linear carbonate-based organic solvent, or a combination thereof.

9. The lithium secondary battery of claim 8, wherein the cyclic carbonate-based organic solvent comprises at least one selected from the group consisting of ethylene carbonate (EC), propylene carbonate (PC), 1,2-butylene carbonate, 2,3-butylene carbonate, 1,2-pentylene carbonate, 2,3-pentylene carbonate, and vinylene carbonate.

10. The lithium secondary battery of claim 8, wherein the linear carbonate-based organic solvent comprises at least one selected from the group consisting of dimethyl carbonate (DMC), diethyl carbonate (DEC), dipropyl carbonate, ethylmethyl carbonate (EMC), methylpropyl carbonate, and ethylpropyl carbonate.

11. The lithium secondary battery of claim 1, wherein the organic solvent comprises a cyclic carbonate-based organic solvent, and a linear carbonate-based organic solvent.

12. The lithium secondary battery of claim 11, wherein the cyclic carbonate-based organic solvent, and the linear carbonate-based organic solvent are included in a ratio of 1:9 to 5:5.

13. The lithium secondary battery of claim 1, wherein the non-aqueous electrolyte solution further comprises at least one additive selected from the group consisting of a halogen-substituted or unsubstituted carbonate-based compound, a sultone-based compound, a sulfate-based compound, a phosphate-based or phosphite-based compound, a borate-based compound, a nitrile-based compound, an amine-based compound, a silane-based compound, and a lithium salt-based compound different from the lithium salt.

14. The lithium secondary battery of claim 1, wherein the positive electrode active material comprises at least one metal selected from the group consisting of nickel (Ni), cobalt (Co), manganese (Mn), iron (Fe), and aluminum (Al), and lithium.

15. The lithium secondary battery of claim 1, wherein the negative electrode active material comprises at least one of a carbon-based negative electrode active material or a silicon-based negative electrode active material.

* * * * *